(12) United States Patent
Afriat

(10) Patent No.: US 6,489,283 B1
(45) Date of Patent: Dec. 3, 2002

(54) COMPOSITION IN THE FORM OF AN OIL-IN-WATER EMULSION CONTAINING FIBERS AND USES THEREOF

(75) Inventor: Isabelle Afriat, Paris (FR)

(73) Assignee: L'Oreal, Paris (FR)

(*) Notice: Subject to any disclaimer, the term of this patent is extended or adjusted under 35 U.S.C. 154(b) by 199 days.

(21) Appl. No.: 09/680,212

(22) Filed: Oct. 6, 2000

(30) Foreign Application Priority Data

Oct. 7, 1999 (FR) .............................. 99 12505

(51) Int. Cl.$^7$ .............................. A61K 7/00; A61K 7/50
(52) U.S. Cl. .................. 510/417; 510/136; 510/137; 510/421; 510/475; 424/401; 424/701
(58) Field of Search ................. 510/137, 136, 510/421, 417, 475; 424/401, 701

(56) References Cited

U.S. PATENT DOCUMENTS

| | | | |
|---|---|---|---|
| 4,970,216 A | * | 11/1990 | Deckner et al. |
| 5,498,407 A | | 3/1996 | Atlas |
| 5,728,389 A | | 3/1998 | Sebillotte-Arnaud |

FOREIGN PATENT DOCUMENTS

| | | |
|---|---|---|
| FR | 7-196440 | 8/1995 |
| JP | 57158714 | 9/1982 |
| JP | 62238211 | 10/1987 |
| JP | 7196440 | 8/1995 |

OTHER PUBLICATIONS

U.S. patent application Ser. No. 09/459,990, filed Dec. 14, 1999, pending.
U.S. patent application Ser. No. 09/453.470, filed Dec. 02, 1999, pending.
U.S. patent application Ser. No. 09/451,918, filed Dec. 01, 1999, pending.
U.S. patent application Ser. No. 09/680,211, filed Oct. 06, 2000, pending.
U.S. patent application Ser. No. 09/688,118, filed Oct. 16, 2000, pending.
U.S. patent application Ser. No. 09/689,768, filed Oct. 16, 2000, pending.
U.S. patent application Ser. No. 09/707,835, filed Nov. 11, 2000, pending.
U.S. patent application Ser. No. 09/680,212, filed Oct. 06, 2000, pending.

* cited by examiner

*Primary Examiner*—Gregory E. Webb
(74) *Attorney, Agent, or Firm*—Oblon, Spivak, McClelland, Maier & Neustadt, P.C.

(57) ABSTRACT

A composition in the form of an oil-in-water emulsion comprising, in a physiologically acceptable medium, an oily phase dispersed in an aqueous phase, characterized in that it contains fibers and a surfactant system comprising at least one glyceryl ester of a $C_8$–$C_{24}$ fatty acid and at least one polyethylene glycol ester of a $C_8$–$C_{24}$ fatty acid. The composition obtained has very good stability and can in particular constitute a cosmetic composition. The invention also relates to the use of the said composition, in particular for caring for, treating, making up or cleansing the skin, the lips, the eyelashes and/or the hair.

12 Claims, No Drawings

COMPOSITION IN THE FORM OF AN OIL-IN-WATER EMULSION CONTAINING FIBERS AND USES THEREOF

BACKGROUND OF THE INVENTION

1. Field of the Invention

The present invention relates to a composition in the form of an oil-in-water emulsion containing fibers and a specific surfactant system, and to the use of the composition, for example, for caring for, treating and/or making up body or facial skin, the hair, the eyelashes and/or the lips.

2. Description of the Background

JP 07-196 440 discloses cosmetic compositions containing short polyamide fibers which give the said compositions a velvety feel and good cosmetic behavior. However, the incorporation of these polyamide fibers into oil-in-water (O/W) emulsions poses problems of stability, i.e. the emulsions dephase at room temperature or at higher temperatures, and do so in particular when the amount of fibers is large.

Thus, is thus still a need for O/W emulsions containing fibers, and in particular polyamide fibers, and which have good cosmetic properties without having the drawbacks of known compositions.

SUMMARY OF THE INVENTION

The Inventor has discovered, unexpectedly, that a surfactant system comprising at least one glycerol ester of a $C_8$–$C_{24}$ fatty acid and at least one polyethylene glycol ester of a $C_8$–$C_{24}$ fatty acid provides a stable oil-in-water emulsions containing fibers.

Thus, the present invention provides a composition in the form of an oil-in-water emulsion comprising, in a physiologically acceptable medium, an oily phase dispersed in an aqueous phase, which contains fibers and a surfactant system comprising at least one glycerol ester of a $C_8$–$C_{24}$ fatty acid and at least one polyethylene glycol ester of a $C_8$–$C_{24}$ fatty acid.

The present invention also provides method of treating, protecting, caring for, removing make-up from and/or cleansing the skin, the lips and/or the hair, and/or for making up the skin, the lips, the eyelashes and/or the body, comprising applying the composition of the invention to the skin, lips, hair, eyelashes and/or body.

The present invention also provides a method of preparing the composition of Claim 1, comprising combining water, at least one oil, the fibers, and the surfactant system.

A more complete appreciation of the invention and many of the attendant advantages thereof will be readily obtained as the same becomes better understood by reference to the following detailed description.

DETAILED DESCRIPTION OF THE INVENTION

The term "physiologically acceptable medium" refers to a medium which is compatible with the skin, the lips, the scalp, the eyelashes, the eyes and/or the hair.

The composition obtained according to the invention is in the form of a cream (soft product as opposed to a solid product). It has good stability over time, even at a temperature above room temperature (for example 45° C.) and it has a velvety texture which feels pleasant when applied.

The fibers which can be used in the composition of the invention can be hydrophilic or hydrophobic fibers of synthetic or natural, and inorganic or organic origin. They can be short or long, individual or organized, for example in bundles. They can have any shape, and in particular a circular or polygonal (square, hexagonal or octagonal) cross section depending on the specific application envisaged. In particular, they have blunt and/or rounded ends to prevent injury.

In particular, the fibers have a length ranging from 1 nm to 20 mm, preferably from 10 nm to 5 mm and better still from 0.1 mm to 1.5 mm. These ranges for the length of the fibers include all specific values and subranges therebetween, such as 5 nm, 25 nm, 50 nm, 0.05 mm, 0.2 mm, 0.5 mm, 1 mm, 2 mm, 10 mm and 15 mm. Their cross section can be within a circle of diameter ranging from 2 nm to 100 µm, preferably ranging from 20 nm to 20 µm and better still from 5 µm to 50 µm. These ranges for the cross sections of the fibers include all specific values and subranges therebetween, such as 5 nm, 10 nm, 50 nm, 1 µm, 2 µm, 10 µm, 25 µm and 50 µm. The weight of the fibers is often given in denier or decitex.

The fibers can be those used in the manufacture of textiles, and in particular silk, cotton, wool or flax fibers. cellulose fibers extracted in particular from wood, plants or algae, polyamide (Nylon®), rayon or viscose fibers, acetate fibers, in particular rayon acetate, poly-p-phenylene terephthamide fibers, in particular Kevlar® fibers, acrylic fibers, in particular polymethyl methacrylate or poly-2-hydroxyethyl methacrylate fibers, polyolefin fibers and in particular polyethylene or polypropylene fibers, glass, silica or aramid fibers, carbon fibers, in particular in graphite form, Teflon®, insoluble collagen, polyester, polyvinyl chloride or polyvinylidene chloride, polyvinyl alcohol, polyacrylonitrile, chitosan, polyurethane or polyethylene phthalate fibers, fibers formed from a mixture of polymers such as those mentioned above, for instance polyamide/polyester fibers.

It is also possible to use fibers used in surgery, such as resorbable synthetic fibers prepared from glycolic acid and from caprolactone (Monocryl from Johnson & Johnson), resorbable synthetic fibers such as the copolymer of lactic acid and of glycolic acid (Vicryl from Johnson & Johnson), terephthalic polyester fibers (Ethibond from Johnson & Johnson) and stainless steel threads (Steel from Johnson & Johnson).

Moreover, the fibers may or may not be surface-treated and may or may not be coated. As coated fibers which can be used in the invention, mention may be made of polyamide fibers coated with copper sulphide for an antistatic effect (for example R-STAT from Rhodia) or another polymer allowing a particular organization of the fibers (specific surface treatment) or a surface treatment which induces color/hologram effects (Lurex fiber from Sildorex, for example).

The fibers which can be used in the composition according to the invention are preferably polyamide and/or poly-p-phenylene terephthamide fibers. Their length can range from 0.1 to 5 mm, preferably from 0.25 to 1.6 mm, and their average diameter can range from 5 to 50 µm. These ranges include all specific values and subranges therebetween, as described above. In particular, the polyamide fibers sold by Etablissements P. Bonte under the name Polyamide 0.9 Dtex 0.3 mm, having an average diameter of 6 µm, a weight of about 0.9 dtex and a length ranging from 0.3 mm to 1.5 mm, can be used. Poly-p-phenylene terephthamide fibers with an average diameter of 12 µm and a length of about 1.5 mm can also be used, such as those sold under the name Kevlar Floc by the company Du Pont Fibers. According to one specific embodiment of the invention, these fibers are introduced in the oily phase of the emulsion.

The fibers can be present in the composition according to the invention in an amount ranging from 0.1 to 20% by weight and preferably from 0.5 to 15% by weight relative to the total weight of the composition. These ranges include all specific values and subranges therebetween, such as 0.2, 1, 2, 5, 10 and 12% by weight relative to the total weight of the composition.

The surfactant system in the emulsion according to the invention comprises at least one glyceryl ester of a $C_8$–$C_{24}$ fatty acid and at least one polyethylene glycol ester of a $C_8$–$C_{24}$ fatty acid.

The glyceryl ester of a fatty acid can be obtained in particular from an acid comprising a saturated linear alkyl chain containing from 8 to 24 and preferably from 16 to 22 carbon atoms. These ranges for the number of carbon atoms include all specific values and subranges therebetween, such as 10, 12, 14, 18 and 20 carbon atoms. Glyceryl esters of a fatty acid which may be mentioned in particular are glyceryl stearate (glyceryl mono-, di- and/or tristearate), glyceryl ricinoleate and their mixtures.

The polyethylene glycol ester of a fatty acid can be obtained in particular from an acid comprising a saturated linear alkyl chain containing from 8 to 24 and preferably from 16 to 22 carbon atoms. These ranges for the number of carbon atoms include all specific values and subranges therebetween, such as 10, 12, 14, 18 and 20 carbon atoms. It can comprise one or more oxyethylenated groups (polyethylene glycol chains: EO) and, for example, from 1 to 150 oxyethylenated groups. This range for the number of oxyethylenated groups includes all specific values and subranges therebetween, such as 5, 10, 25, 50, 80, 100 and 125 oxyethylenated groups. Polyethylene glycol esters of a fatty acid which may be mentioned in particular are polyethylene glycol stearate (polyethylene glycol mono-, di- and/or tristearate) and more especially polyethylene glycol monostearate 50 EO (CTFA name: PEG-50 stearate).

The glycerol ester of a fatty acid can be present in an amount preferably ranging from 0.5% to 5% by weight and better still from 2% to 3% by weight relative to the total weight of the composition. These ranges include all specific values and subranges therebetween, such as 1.5, 2.5, 4 and 4.5% by weight relative to the total weight of the composition.

The polyethylene glycol ester of a fatty acid can be present in an amount preferably ranging from 0.5% to 5% by weight and better still from 2% to 3% by weight relative to the total weight of the composition. These ranges include all specific values and subranges therebetween, such as 1.5, 2.5, 4 and 4.5% by weight relative to the total weight of the composition.

The surfactant system is present overall in the composition according to the invention in an amount ranging from 1% to 10% by weight, preferably 4% to 6% by weight, relative to the total weight of the composition. These ranges include all specific values and subranges therebetween, such as 2, 5 and 8% by weight relative to the total weight of the composition. This surfactant system is generally incorporated into the oily phase.

The oily phase of the composition according to the invention generally represents from 10% to 50% and preferably from 15% to 30% by weight relative to the total weight of the composition. These ranges include all specific values and subranges therebetween, such as 20, 25, 35, 40 and 45% by weight relative to the total weight of the composition.

The oily phase can consist of any fatty substance and in particular any oil conventionally used in cosmetics or dermatology.

Among the oils which may be used in the emulsion of the invention, mention may be made, for example, of plant oils such as jojoba oil, avocado oil, sweet almond oil, apricot oil, corn oil and the liquid fraction of karite butter; mineral oils, for instance liquid petroleum jelly and hydrogenated polyisobutene (parleam oil); synthetic oils, for instance 2-ethylhexyl palmitate, isopropyl myristate, hydrogenated isoparaffin, isononyl isononanoate or cetearyl octanoate; volatile or non-volatile silicone oils and fluoro oils. The other fatty substances which may be present in the oily phase may be, for example, fatty acids and fatty alcohols such as cetyl alcohol.

The aqueous phase of the composition of the invention generally constitutes from 50% to 90% and preferably from 60% to 80% by weight relative to the total weight of the composition. These ranges include all specific values and subranges therebetween, such as 55, 65, 70, 75 and 85% by weight relative to the total weight of the composition.

In a known manner, the compositions of the invention can contain adjuvants that are common in the fields under consideration, such as hydrophilic or lipophilic active agents, preserving agents, gelling agents, antioxidants, fragrances, solvents, fillers or nacres, screening agents, dyestuffs (soluble dyes or pigments), basic or acidic agents, as well as lipid vesicles. These adjuvants are used in the proportions that are usual in cosmetics, and, for example, from 0.01% to 30% relative to the total weight of the emulsion, and, depending on their nature, they are introduced into the aqueous phase or into the oily phase of the emulsion, or alternatively into vesicles. These adjuvants and their concentrations should be such that they do not modify the property desired for the emulsion of the invention.

Active agents which may be mentioned, for example, are moisturizers such as polyols, for instance glycerol and sorbitol; keratolytic agents; depigmenting agents; weight-reducing agents and any active agent which is suitable for the final aim of the composition.

Depending on the fluidity of the composition which it is desired to obtain, one or more hydrophilic or lipophilic gelling agents may be added thereto. Hydrophilic gelling agents which may be mentioned, for example, are carboxyvinyl polymers such as carbomers. Lipophilic gelling agents which may be mentioned are modified clays such as bentones, such as the mixture "cyclomethicone, Quaternium-18 hectorite, and SD alcohol 40" (10/85/5) (CTFA name) sold under the name Bencone Gel VS-5 by Rheox; crosslinked elastomeric polyorganosiloxanes such as those marketed under the names KSG6 from Shin-Etsu, Trefil E-505C or Trefil E-506C from Dow-Corning, Gransil from Grant Industries (SR-CYC, SR DMF10, SR-DC556), or those sold in the form of gels: KSG15, KSG17, KSG16 and KSG18 from Shin-Etsu, Gransil SR 5CYC gel, Gransil SR DMF 10 gel, Gransil SR DC 556 gel and SF 1204 and JK 113 from General Electric.

When they are present, these gelling agents are generally used at concentrations ranging from 0.1% to 7% and preferably from 0.1% to 5% by weight of active material relative to the total weight of the composition. These ranges include all specific values and subranges therebetween, such as 0.2, 0.5, 1, 2 and 3% by weight relative to the total weight of the composition.

The compositions, which are the subject of the invention, find their application in a large number of treatments, in particular cosmetic treatments, and can thus constitute a cosmetic composition, in particular for treating, protecting, caring for, removing make-up from and/or cleansing the skin, the lips and/or the hair, and/or for making up the skin, the lips, the eyelashes and/or the body.

The compositions according to the invention can be used, for example, as care products, make-up-removing products and/or cleansing products for the face in the form of creams or milks, or as make-up products (for the skin, eyelashes and lips) by incorporating pigments or dyes, for example such as foundations.

Thus, a the present invention includes the cosmetic use of the composition as defined above for treating, protecting, caring for, removing make-up from and/or cleansing the skin, the lips and/or the hair, and/or for making up the skin, the lips, the eyelashes and/or the body.

The present invention also includes a cosmetic treatment process for the skin, including the scalp, the hair, the eyelashes and/or the lips, characterized in that a composition as defined above is applied to the skin, the eyelashes and/or the lips.

EXAMPLES

Having generally described this invention, a further understanding can be obtained by reference to certain specific examples which are provided herein for purposes of illustration only and are not intended to be limiting unless otherwise specified. The amounts indicated are percentages by weight, except where otherwise mentioned.

Example 1

| Protective Day Cream | |
|---|---|
| Oily phase | |
| Liquid petroleum jelly | 6.2% |
| Isopropyl myristate | 3% |
| Cetyl alcohol | 7% |
| Glyceryl stearate | 2.5% |
| PEG-50 stearate | 2.5% |
| Aqueous phase: | |
| Preserving agents | 0.3% |
| Demineralized water | qs 100% |
| Polyamide fibers (Polyamide 0.9 Dtex, 0.3 mm - Paul Bonte company) | 10% |

Procedure: The oily phase is heated until it is homogeneous and the fibers are then added thereto. The mixture obtained is then poured into the aqueous phase, which has been preheated to the same temperature, with vigorous stirring.

A cream is obtained which remains stable over time, even after storage at 45° C. When applied to the skin, it affords great softness and is particularly suitable for making the skin supple.

Example 2

| Protective Day Cream | |
|---|---|
| Oily phase | |
| Parleam oil | 6.2% |
| Isopropyl myristate | 3% |
| Cetyl alcohol | 7% |
| Glyceryl stearate | 2.5% |
| PEG-50 stearate | 2.5% |

| Protective Day Cream | |
|---|---|
| Aqueous phase: | |
| Preserving agents | 0.3% |
| Demineralized water | qs 100% |
| Polyamide fibers | 10% |

(Polyamide 0.9 Dtex, 0.3 mm - Paul Bonte company)

The procedure is the same as that of Example 1.

A cream which is capable of moisturizing the skin is obtained.

Example 3

| Protective Day Cream | |
|---|---|
| Oily phase | |
| Apricot oil | 6.2% |
| Isopropyl myristate | 3% |
| Cetyl alcohol | 7% |
| Glyceryl stearate | 2.5% |
| PEG-50 stearate | 2.5% |
| Aqueous phase: | |
| Preserving agents | 0.3% |
| Demineralized water | qs 100% |
| Polyamide fibers (Polyamide 0.9 Dtex, 0.3 mm - Paul Bonte company) | 10% |

The procedure is the same as that of Example 1.

A cream which makes the skin soft is obtained.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 9912505, filed on Oct. 7, 1999, the contents of which are incorporated herein by reference.

What is claimed is:

1. A composition in the form of a oil-in-water emulsion form comprising in a physiologically acceptable medium:
   an oily phase dispersed in an aqueous phase, fibers, and
   a surfactant system comprising at least one glycerol ester of a $C_8$–$C_{24}$ fatty acid and at least one polyethylene glycol ester of a $C_8$–$C_{24}$ fatty acid.

2. The composition of claim 1, wherein the fibers have a length ranging from 0.1 mm to 5 mm.

3. The composition of claim 1, wherein the fibers have a cross section within a circle of diameter ranging from 5 $\mu$m to 50 $\mu$m.

4. The composition of claim 1, wherein the fibers are selected from the group consisting of polyamide fibers, poly-p-phenylene terephthamide fibers and mixtures thereof.

5. The composition of claim 1, wherein the fibers are present in an amount ranging from 0.1 to 15% by weight relative to the total weight of the composition.

6. The composition of claim 1, wherein the glycerol ester of a fatty acid is selected from the group consisting of glyceryl mono-, di- and/or tristearate and glyceryl ricinoleate, and mixtures thereof.

7. The composition of claim 1, wherein the polyethylene glycol ester of a fatty acid comprises from 1 to 150 oxyethylenated groups.

8. The composition of claim 1, wherein the surfactant system is present in an amount ranging from 1 to 10% by weight relative to the total weight of the composition.

9. The composition of claim 1, wherein the oily phase represents from 10 to 50% by weight relative to the total weight of the composition.

10. The composition of claim 1, wherein the composition constitutes a cosmetic composition.

11. A method of treating, protecting, caring for, removing make-up from and/or cleansing the skin, the lips and/or the hair, and/or for making up the skin, the lips, the eyelashes and/or the body, comprising applying the composition of claim 1 to the skin, lips, hair, eyelashes and/or body.

12. A method of preparing the composition of claim 1, comprising combining water, at least one oil, the fibers, and the surfactant system.

* * * * *